United States Patent
Leyde

[19]

[11] Patent Number: 6,104,953
[45] Date of Patent: Aug. 15, 2000

[54] METHOD AND APPARATUS FOR DELIVERING DEFIBRILLATION AND PACING ENERGY FROM A SINGLE POWER SOURCE

[75] Inventor: Kent W Leyde, Redmond, Wash.

[73] Assignee: Heartstream, Inc., Seattle, Wash.

[21] Appl. No.: 09/239,408

[22] Filed: Jan. 28, 1999

[51] Int. Cl.[7] ............................................. A61N 1/39
[52] U.S. Cl. ............................................................ 607/4
[58] Field of Search .................................... 607/4, 5, 6, 7, 607/8

[56] References Cited

U.S. PATENT DOCUMENTS

| | | |
|---|---|---|
| 4,504,773 | 3/1985 | Suzuki et al. . |
| 4,637,397 | 1/1987 | Jones et al. . |
| 4,745,923 | 5/1988 | Winstrom . |
| 4,850,357 | 7/1989 | Bach, Jr. . |
| 4,953,551 | 9/1990 | Mehra et al. . |
| 4,998,531 | 3/1991 | Bocchi et al. . |
| 5,078,134 | 1/1992 | Heilman et al. . |
| 5,083,562 | 1/1992 | De Coriolis et al. . |
| 5,111,816 | 5/1992 | Pless et al. . |
| 5,222,492 | 6/1993 | Morgan et al. . |
| 5,230,336 | 7/1993 | Fain et al. . |
| 5,249,573 | 10/1993 | Fincke et al. . |
| 5,395,394 | 3/1995 | Cameron et al. . |
| 5,443,490 | 8/1995 | Flugstad . |
| 5,472,454 | 12/1995 | Ozawa . |
| 5,594,287 | 1/1997 | Cameron . |

FOREIGN PATENT DOCUMENTS

| | | |
|---|---|---|
| WO/93/16759 | 9/1993 | WIPO . |
| WO/94/22530 | 10/1994 | WIPO . |

*Primary Examiner*—Scott M. Getzow
*Attorney, Agent, or Firm*—Cecily Anne Snyder

[57] ABSTRACT

A defibrillator circuit that delivers high voltage electrical pulses and lower energy pacing pulses to a patient. The circuit allows the patient to be isolated so that no current leaks prior to the administration of the pacing or defibrillation pulse. In one embodiment, the delivery circuit includes a high voltage capacitor, with a GTO selectively connecting the positive terminal of the capacitor to ground. The negative terminal of the capacitor is coupled to one terminal of a bridge circuit, and another terminal of the bridge circuit is connected to ground. The bridge circuit has four SCRs which are selectively switched to produce the biphasic steering of current. Current conduction through the bridge circuit is initiated and commutated by the GTO. Turning on the GTO connects the positive terminal of the charged capacitor to ground, thereby lowering the potential of the negative terminal and causing current flow through the bridge circuit. By avoiding application of the capacitor voltage to the bridge circuit prior to energy discharge there through, a number of advantages are achieved over conventional defibrillator circuit designs.

31 Claims, 7 Drawing Sheets

METHOD AND APPARATUS FOR DELIVERING DEFIBRILLATION AND PACING ENERGY FROM A SINGLE POWER SOURCE

TECHNICAL FIELD

This invention relates to a method and apparatus for delivering electrical energy produced by a defibrillator to a patient experiencing ventricular fibrillation ("VF"). In one embodiment, a single power source is provided that allows delivery of either pacing or defibrillation energy. This invention may be used with either implantable or external defibrillators. External defibrillators include automatic or semi-automatic external defibrillators ("AED"), manual defibrillators and trainers.

BACKGROUND OF THE INVENTION

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated that more than 1000 people per day are victims of SCA in the United States alone.

SCA occurs when the heart stops pumping blood. Usually SCA is due to abnormal electrical activity in the heart, resulting in an abnormal rhythm (arrhythmia). One such abnormal rhythm, VF, is caused by abnormal and very fast electrical activity in the heart. During VF the heart cannot pump blood effectively. Because blood may no longer be pumping effectively during VF, the chances of surviving decrease with time after the onset of the emergency. Brain damage can occur after the brain is deprived of oxygen for four to six minutes.

VF is treated by applying an electric shock to the patient's heart through the use of a defibrillator. The shock clears the heart of the abnormal electrical activity (in a process called "defibrillation") by depolarizing a critical mass of myocardial cells to allow spontaneous organized myocardial depolarization to resume.

Other forms of abnormal cardiac rhythms, such as bradycardia (slow heart rate) and tachycardia (rapid heart rate) can be treated with a low voltage pacing pulse, which assists the heart's natural pacemakers.

External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, AEDs are becoming increasingly popular because they can be used by relatively inexperienced personnel. Such defibrillators can also be especially lightweight, compact, and portable. Because of the lightweight and portable nature of currently available AEDs it would be desirable to add additional features, such as pacing in order to increase the number of cardiac emergencies the device can treat. Unfortunately, the addition of such advanced features also requires the addition of circuitry to accommodate the features. This additional circuitry necessarily increases the weight and size of the defibrillator, thus reducing the compactness and portability. For example, currently available defibrillators with pacing capabilities typically includes two power sources, two capacitors, and two control mechanisms—one for the high energy defibrillation pulse and one for the lower energy pacing pulses. This double circuitry ultimately increases the weight and size of the device.

What is needed, therefore, is a defibrillator capable of pacing which uses a single power source, a single high energy capacitor and a single control mechanism to deliver either defibrillation or pacing energy.

SUMMARY OF THE INVENTION

An electrical energy delivery circuit is provided for defibrillating a patient experiencing VF. The delivery circuit includes a storage circuit for storing electrical energy and having first and second terminals. The storage circuit may be coupled between a first reference voltage and a second reference voltage, wherein the second reference voltage is the bridge. A steering circuit is coupled with the first terminal of the storage circuit. The steering circuit is for coupling with the patient to transfer the electrical energy stored in the storage circuit to the patient. A discharge control circuit is coupled with the second terminal of the storage circuit and is operable to electrically isolate the second terminal of the storage circuit from the steering circuit. The discharge control circuit is also operable to electrically connect the second terminal of the storage circuit with the steering circuit to initiate delivery of the electrical energy to the patient through the steering circuit.

In one embodiment, the storage circuit may be a capacitor, the steering circuit may be a bridge circuit having a plurality of electrically controlled switching elements, and the discharge control circuit may be an electrically controlled switch. The discharge control circuit operates to initially electrically isolate the bridge circuit from the capacitor voltage, and to subsequently initiate and control energy transfer from the capacitor to the bridge circuit. By avoiding application of the capacitor voltage to the bridge circuit prior to energy discharge therethrough, a number of advantages are achieved over conventional defibrillator circuit designs.

DETAILED DESCRIPTION OF THE INVENTION

Currently available external defibrillators provide either a monophasic or biphasic electrical pulse to a patient through electrodes applied to the chest. Additionally, defibrillators may provide high energy defibrillating pulses or lower energy pacing pulses. Monophasic defibrillators deliver an electrical pulse of current in one direction. Biphasic defibrillators deliver an electrical pulse of current first in one direction and then in the opposite direction. When delivered external to the patient, these electrical pulses are high energy (typically in the range of 30 J to 360 J). This invention may be employed by defibrillators that generate monophasic, biphasic or multiphasic waveforms. Additionally this invention may be employed by defibrillators that allow the user to select the waveform type. Finally, this invention may be employed in either external or implantable defibrillators.

Defibrillators employing a monophasic waveform are well known in the art. While this invention may be used with a defibrillator employing a monophasic waveform, it is believed that the solution described herein is primarily beneficial for defibrillators that deliver biphasic or multiphasic waveforms, and more specifically defibrillators that combine defibrillation with pacing. An example of a circuit used for discharging a capacitor delivering a monophasic waveform is described in U.S. Pat. No. 4,504,773 (Suzuki et al.).

In accordance with the present invention, embodiments of defibrillators are provided that have a high voltage bridge circuit using only four switching elements to steer the biphasic pulse. Separate from the bridge circuit, a fifth switching element is provided for current initiation and commutation control, and a sixth switching element is provided for discharging/disarming the energy storage capacitor in the event of a fault. In the following description, certain specific details are set forth in order to provide a thorough understanding of embodiments of the present invention. It will be clear, however, to one skilled in the art, that the present invention can be practiced without these details. In other instances, well-known circuits have not been shown in detail in order to avoid unnecessarily obscuring the description of the various embodiments of the invention. Also not presented in any great detail are those well-known control signals and signal timing protocols associated with the internal operation of defibrillators.

Figure 1:
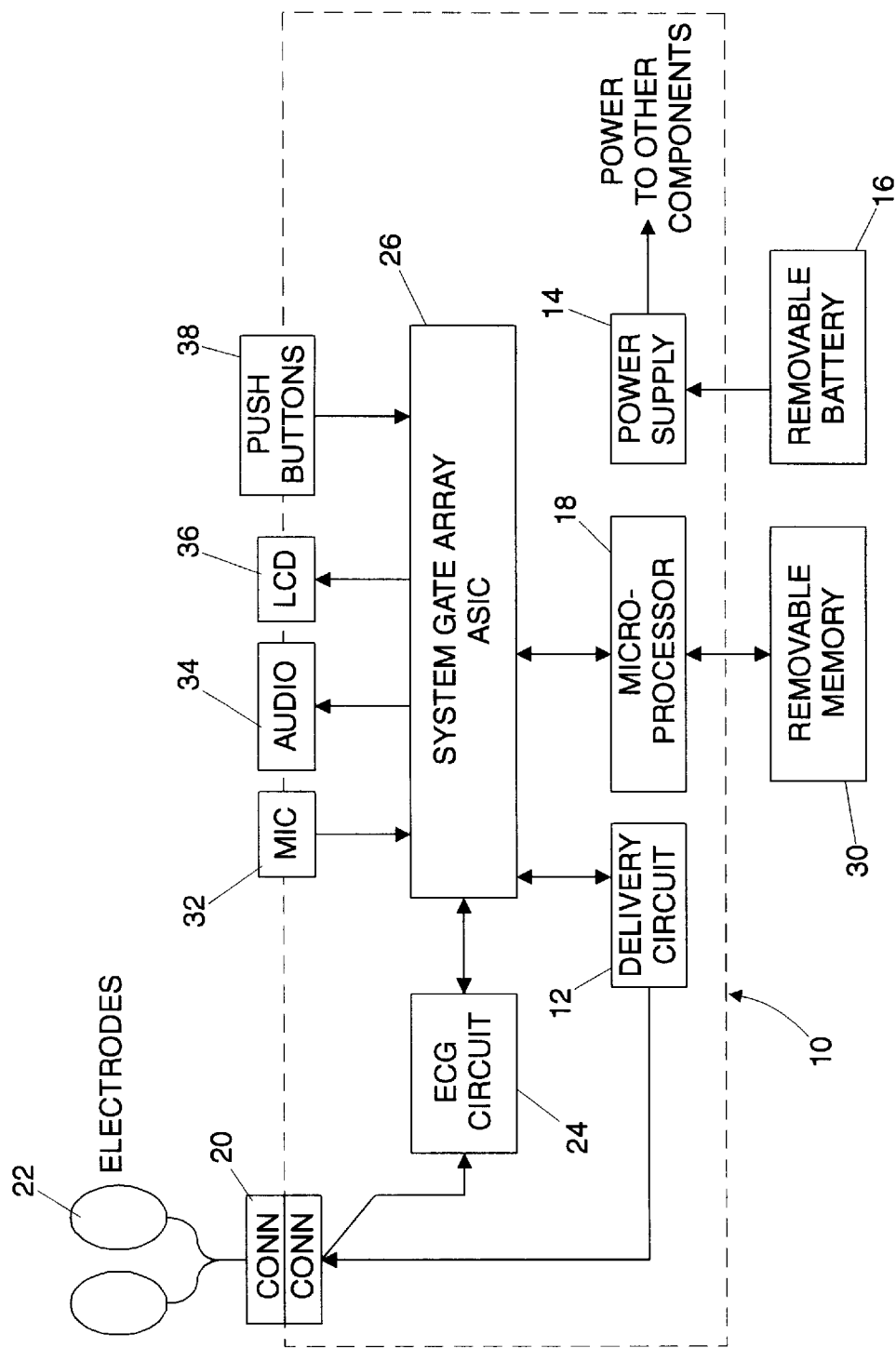
FIG. 1 is a functional block diagram depicting an external defibrillator according to an embodiment of the present invention.

FIG. 1 is a functional block diagram depicting a defibrillator or AED 10 having a delivery circuit 12, capable of delivering high or low voltage, depending upon the application, in accordance with an embodiment of the present invention. The AED 10 includes a power supply 14, which is powered by an energy source such as a removable battery 16 and provides power to other components of the AED. A microcontroller or processor 18 controls the operation of the various components of the AED 10. The high-voltage delivery circuit 12 delivers a pulse of electrical energy to a patient via an electrode connector or interface 20 and electrodes 22.

An electrocardiogram (ECG) circuit 24 acquires and processes the patient's ECG signals through the electrodes 22 and sends the signals to the processor 18 via a system gate array 26. The system gate array 26 is a custom application-specific integrated circuit (ASIC) integrating many of the defibrillator functions (including user interface control and many of the internal functions) and interfacing the processor 18 with other components of the AED 10. Providing the separate system gate array or ASIC 26 allows the processor 18 to focus on other tasks. Of course, the functionality of the ASIC 26 could be included within the operations performed by the processor 18, or could be replaced by discrete logic circuit components or a separately dedicated processor.

The AED 10 also includes a memory device 30 (such as a removable Personal Computer Memory Card International Association ("PCMCIA") card or magnetic tape), and user interface components such as a microphone 32, an audio speaker 34, an LCD display panel 36, and a set of push-button controls 38. Those skilled in the art will understand that a number of other components are included within the AED 10 (e.g., a system monitor and associated status indicators), but are not shown in order to avoid unnecessarily obscuring the description of embodiments of the invention.

Figure 2:
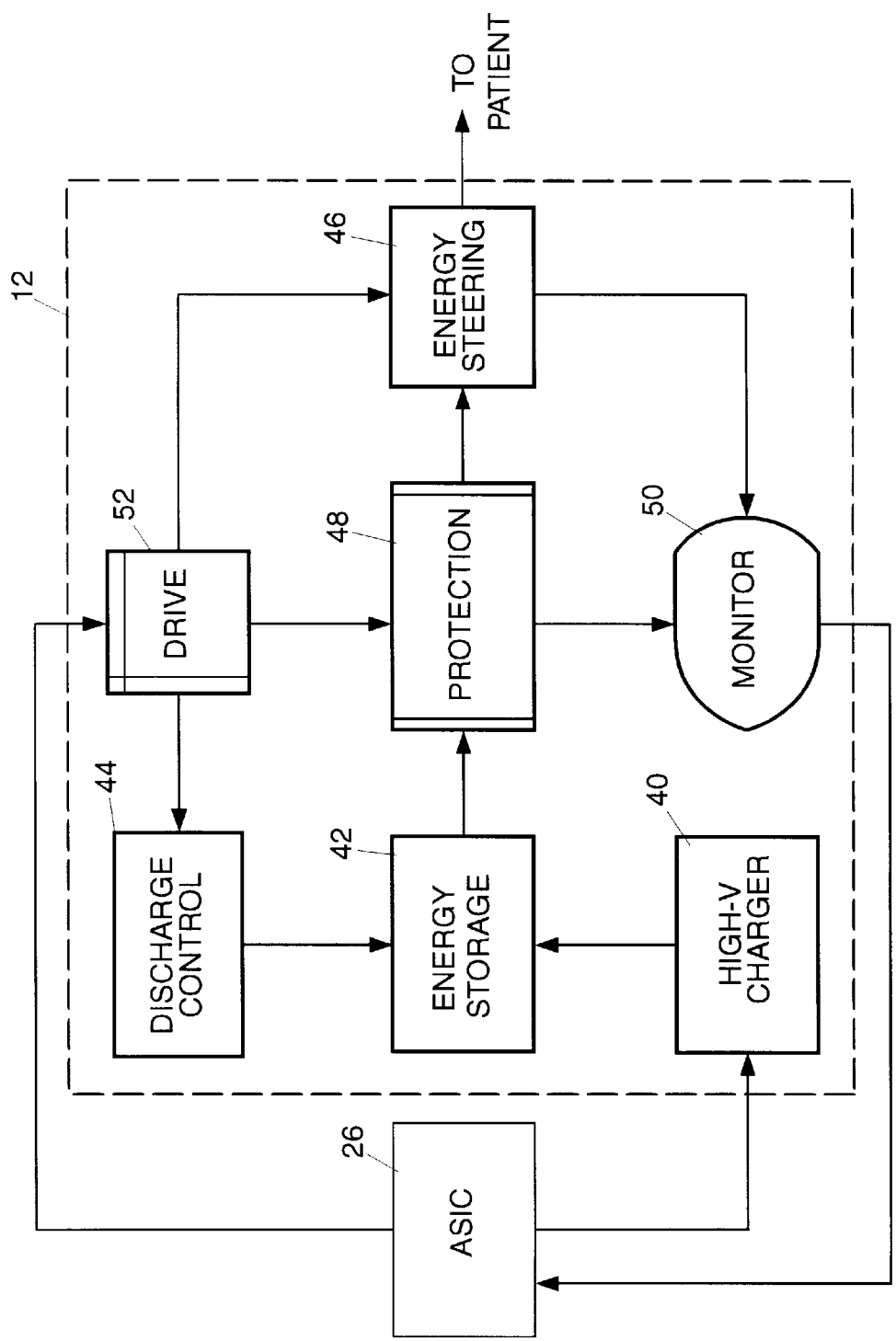
FIG. 2 is a functional block diagram depicting a high-voltage delivery circuit included in the defibrillator of FIG. 1.

As shown in FIG. 2, the high-voltage delivery circuit 12 includes a number of functional circuit blocks which are both monitored and controlled by the ASIC 26. A high-voltage charging circuit 40, such as a flyback power supply, responds to one or more control signals issued by the ASIC 26 and generates electrical energy for provision to an energy storage circuit 42. The storage circuit 42 stores the electrical energy for subsequent delivery to the patient. A discharge control circuit 44 controls discharge of the energy stored in the storage circuit 42 to an energy transfer or steering circuit 46 through a protection circuit 48. The steering circuit 46 in turn delivers the electrical energy to the patient via the connector 20 and electrodes 22 (shown in FIG. 1). The steering circuit 46 may deliver the electrical energy to the patient with a single polarity (e.g., a monophasic pulse) or with an alternating polarity (e.g., a biphasic or multiphasic pulse), as required by the desired implementation.

The protection circuit 48 functions to limit energy delivery from the storage circuit 42 to the steering circuit 46 (and hence to the patient) and to discharge or otherwise disarm the storage circuit 42 in the event of a fault condition. The protection circuit 48 operates to limit the time-rate-of-change of the current flowing through the bridge circuit. A monitor circuit 50 senses operations of both the protection circuit 48 and the steering circuit 46 and reports the results of such monitoring to the ASIC 26. The above-described operations of the discharge control circuit 44, the steering circuit 46, and the protection circuit 48 are controlled by a drive circuit 52 issuing a plurality of drive signals. Operation of the drive circuit 52 is, in turn, controlled by one or more control signals provided by the ASIC 26.

Although it is contemplated that this invention may be employed with implantable and external defibrillators, the invention has been described primarily in terms of an external defibrillator in order to clearly illustrate the invention. Persons of skill in the art would be able to modify the threshold values for components for application in an implantable defibrillator, without undue experimentation.

Figure 3A:
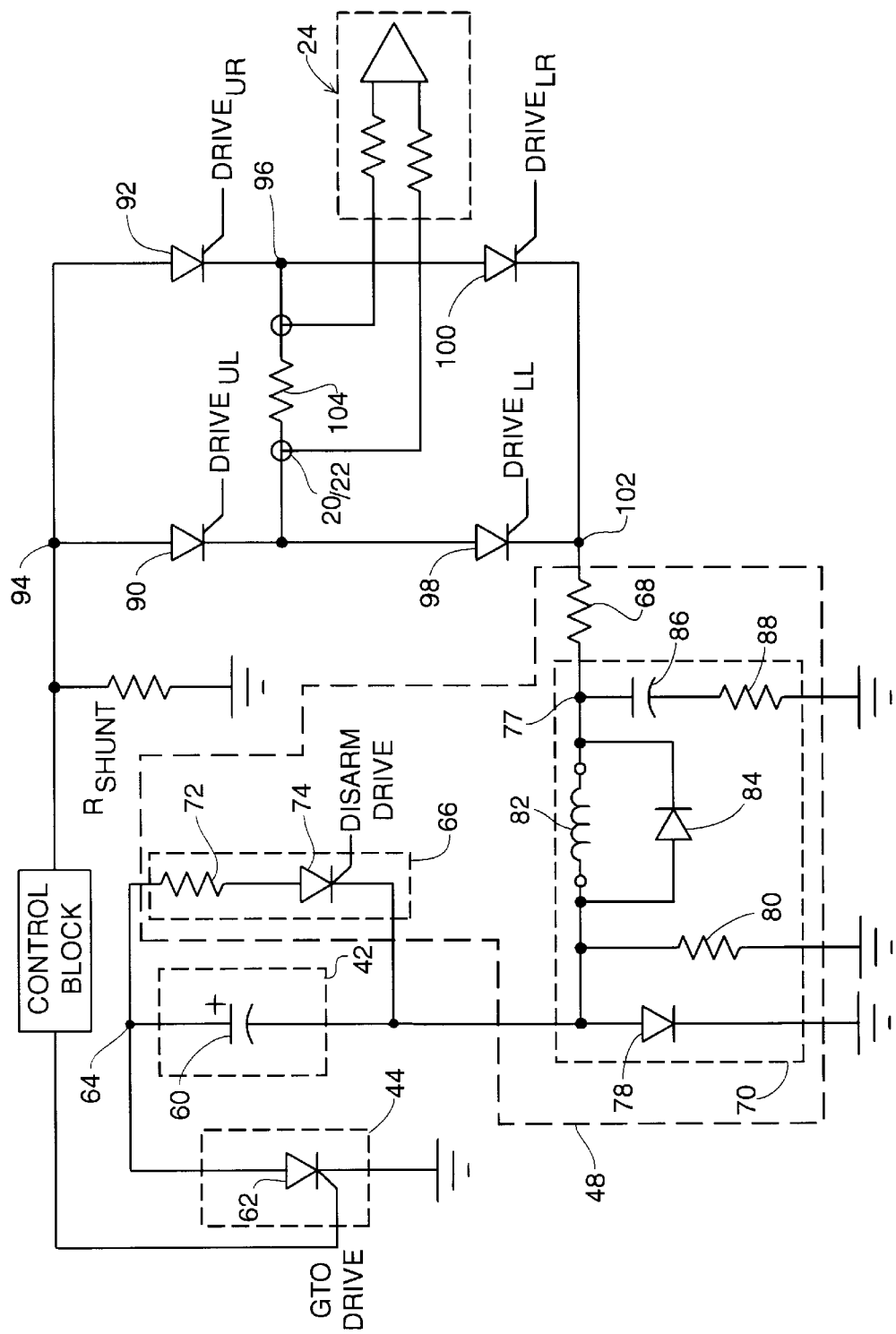
FIG. 3A is a schematic diagram depicting certain details of a first embodiment of the defibrillation and pacing circuit of FIG. 2.

FIG. 3A depicts embodiments of the storage circuit 42, discharge control circuit 44, steering circuit 46, and protection circuit 48. The energy storage circuit 42 is a storage capacitor (or a multiple capacitor unit) 60, with a suitable capacitance being approximately 100 $\mu$F and being capable of regularly and reliably storing energy at approximately 2200 V for external defibrillation. The discharge control circuit 44 is a gate-assist turnoff switch (GTO) 62. The GTO 62 has its anode connected with a positive terminal or node 64 of the capacitor 60. The cathode of the GTO 62 is coupled to a reference voltage source, such as ground potential.

A resistor $R_{SHUNT}$ is provided in series with ground to allow sensing of patient current. Typically $R_{SHUNT}$ has a value of 50 m$\Omega$. The control terminal or gate of the GTO 62 receives a GTO drive signal provided by the drive circuit 52 (shown in FIG. 2) to selectively couple the positive terminal 64 of the capacitor 60 to ground.

Figure 3B:
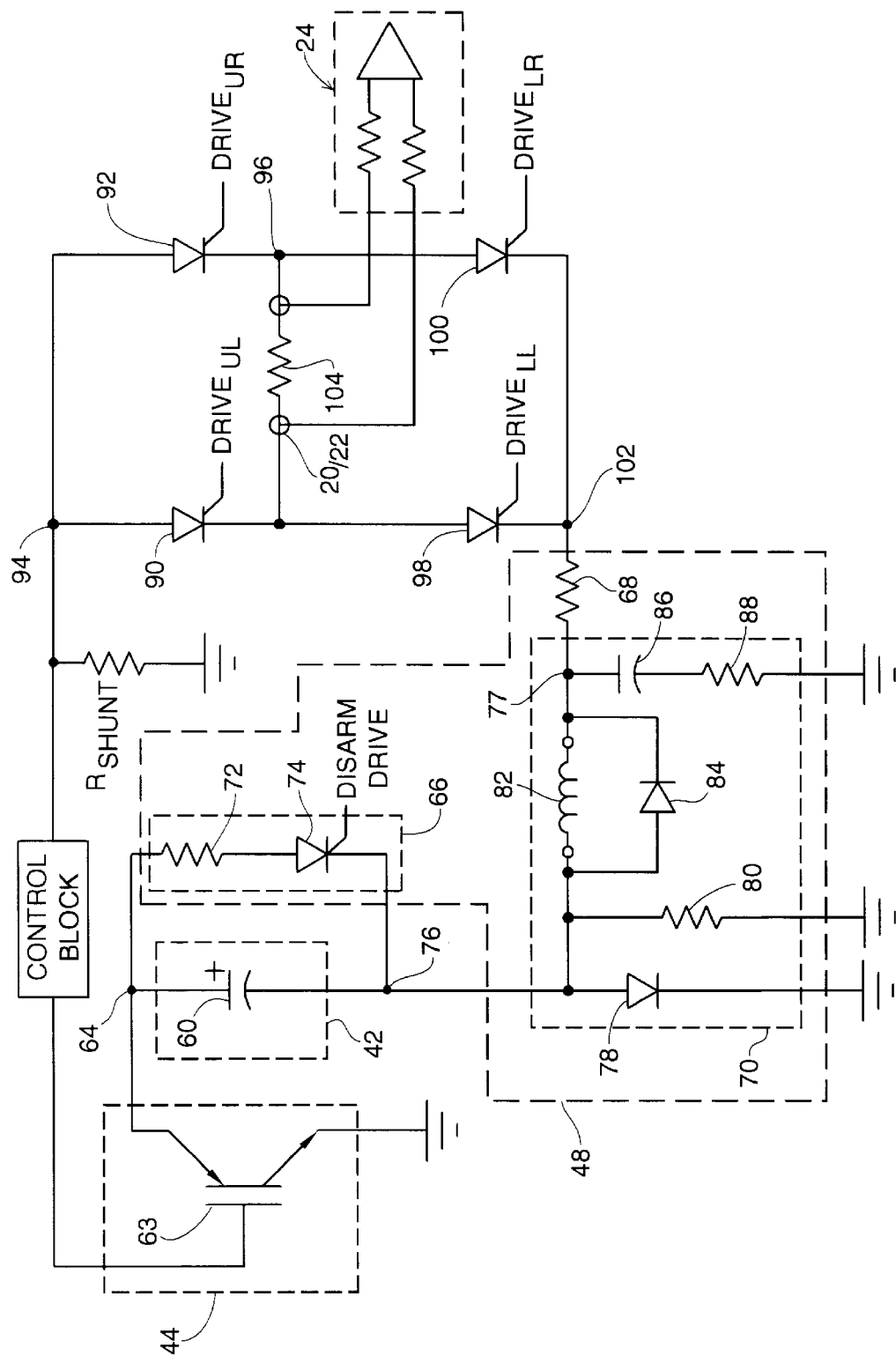
FIG. 3B is a schematic diagram depicting an alternative embodiment of the circuit shown in FIG. 3A.

The protection circuit 48 of FIG. 2 is shown in FIGS. 3A and 3B as three distinct subcircuits—namely, a disarm circuit 66, a current limiting resistor 68, and a snubber circuit 70. The disarm circuit 66 includes a disarm resistor 72 (with a suitable resistance value being approximately 20 $\Omega$, more preferably 10 $\Omega$ and a silicon-controlled rectifier switch (SCR) 74. The disarm resistor 72 and SCR 74 are connected in series between the positive terminal 64 and a negative terminal or node 76 of the storage capacitor 60. If a fault condition is detected, the disarm SCR 74 can be switched on and the energy stored in the capacitor 60 substantially dissipated in the disarm resistor 72. The disarm SCR 74 is selectively switched on by a disarm drive signal provided by the drive circuitry 52 (shown in FIG. 2).

The current limiting resistor 68 is in series with the snubber circuit 70 between node 77 and node 102. The current limiting resistor 68 limits maximum current flow, with a suitable resistance value being in the range of approximately 3–15 Ω, more preferably 3–5 Ω. As a practical matter, monitoring current flow through the damping resistor 80 is most appropriate during capacitor charging operations, when the currents (and voltage across the protection resistor) are relatively modest. The currents associated with patient defibrillation are such that a significantly smaller resistor is desirable for current monitoring. For example, the monitor circuitry 50 (FIG. 2) could monitor the voltage drop across a 0.05 Ω resistor (not shown) during patient defibrillation to provide information to the ASIC 26 concerning defibrillation current.

The snubber circuit 70 includes a ground return path clamping diode 78 and damping resistor 80. The clamping diode 78 keeps the voltage of the node 77 approximately at or below ground potential, while the ground return damping resistor 80 keeps the voltage of the node 77 approximately at ground potential during capacitor charging and stand-by operations. The snubber circuit 70 also includes traditional snubber circuitry for limiting the time rate of change of current and for smoothing the signal transmitted therethrough. Such circuitry includes an inductor 82 with associated flyback diode 84, and filtering capacitor 86 and resistor 88. Suitable resistance values for the damping resistors 80 and 88 are approximately 2 kΩ and 50 Ω, respectively, for an external defibrillator. Suitable values for the inductor 82 and the capacitor 86 are approximately 75 μH and 20 nF, respectively, for an external defibrillator. A suitable choice for each of the diodes 78 and 84 shown in FIG. 3 is a Z25UFG diode. In operation, the monitor circuitry 50 (of FIG. 2) can advantageously monitor the voltage drop across damping resistor 80 to correspondingly provide information to the ASIC 26 concerning current flow.

The energy steering circuit 46 is of an "H-bridge" configuration, with four switching elements. The steering circuit 46 includes an upper-left (UL) switching element, such as SCR 90, and an upper-right (UR) switching element, such as SCR 92. The anode of each of the SCRs 90, 92 is connected to a reference voltage source, such as ground potential, in series with $R_{SHUNT}$ at an upper terminal or node 94. The cathode of each of the SCRs 90, 92 is connected to a respective one of two patient terminals 96 (which, in turn, are coupled with the connector 20 and a respective electrode 22 of FIG. 1). The control terminal or gate of each of the SCRs 90, 92 receives an UL or UR drive signal produced by the drive circuit 52 (shown in FIG. 2) to selectively switch the SCRs on. A patient is represented by a resistor 104, shown in the electrical location of the patient during circuit operation. Additionally, a functional block representation of a portion of the ECG circuitry 24 of FIG. 1 is depicted.

The steering circuit 46 also includes a lower-left (LL) switching element, such as SCR 98, and a lower-right (LR) switching element, such as SCR 100. The anode of each of the SCRs 98, 100 is connected to one of the patient terminals 96. The cathode of each of the SCRs 98, 100 is connected to a lower terminal or node 102. The control terminal or gate of each of the SCRs 98, 100 receives a LL or LR drive signal from the drive circuit 52 (shown in FIG. 2) to selectively switch the SCRs on. As desired, the monitor circuitry 50 of FIG. 2 can advantageously sense the voltage of the node 102 and provide such information to the ASIC 26. Alternatively, time integration of monitored current flow can provide information corresponding to voltages during patient defibrillation.

The above-described control signals applied to the gates of the SCRs 74, 90, 92, 98, 100 may each be suitably provided by a corresponding pulse transformer. The secondary coil of each of the transformers may be tied directly to the corresponding SCR gate, with the SCRs designed so that, once triggered and conducting, they will tolerate the short-circuit on the gate-cathode junction that occurs with transformer saturation. The GTO 62 may be suitably controlled by a 5 volt system, with a 5 volt pulse used to turn on the GTO and a logic-level MOSFET (such as a very low on-resistance n-channel device) used to turn off the GTO.

The SCRs 74, 90, 92, 98, 100 are preferably not of the type commonly used in power supplies or motor control, in which switching efficiency parameters such as forward voltage drop, fast switching times, reduced current tails, average current capability, average power dissipation, etc. are considered important. The SCRs 90, 92, 98, 100 are used primarily to steer current, and do not experience the power dissipation associated with more conventional switching applications of SCRs. The SCRs 90, 92, 98, 100 steer a current pulse, and their ability to handle very low duty cycle transients is more important than average power dissipation efficiencies. Accordingly, conventional SCR design rules may be relaxed or otherwise modified, such as by allowing considerably lighter semiconductor doping levels, as will be understood by those skilled in the art.

A variety of SCRs are suitable for use in this application provided the SCR has a 2500 V forward and reverse blocking voltage. Additionally, a variety of GTOs are suitable for use in this application provided that the peak forward blocking voltage is from 2000 to 2500 V. Those skilled in the art will readily understand, however, that circuits may be constructed according to the present invention with components having other, suitably matched device parameters.

In the preferred embodiment, shown in FIG. 3B, GTO drive of the discharge control circuit 44 may be replaced by an insulated gate bipolar transistor ("IGBT"). The IGBT 63 has its collector connected with a positive terminal or node 64 of the capacitor 60. The emitter of the IGBT 63 is coupled to a reference voltage source, such a ground potential. A resistor $R_{SHUNT}$ is provided in series with ground to allow sensing of patient current. Typically $R_{SHUNT}$ has a value of 50 mΩ. The control terminal or gate of the IGBT 63 receives a signal provided by the drive circuit 52 (shown in FIG. 2) to selectively couple the positive terminal of the capacitor 60 to ground. While functionally performing the same step, the advantage of using an IGBT instead of an GTO is that the IGBT is controllable over a wider range of current. Additionally IGBTs are widely available.

The operation of the circuit structure shown in FIGS. 3A and B will now be described. The storage capacitor 60 is charged by the charging circuitry 40 (shown in FIG. 2), with the positive terminal 64 having a positive voltage relative to the negative terminal 76. Depending upon whether the defibrillator is used for pacing or defibrillation, the capacitor will be charged to 100 V to 2000V. During stand-by operations, the capacitor 60 is fully charged, but no energy is delivered to the patient resistance 104, pending completion of ECG monitoring by the ECG circuit 24. The ECG circuit 24 is typically ground referenced, and the patient terminals are therefore substantially at ground potential during stand-by operations. During this time, the GTO 62 and the disarm SCR 74 are off, with any leakage current through the GTO being returned by the ground return diode 78 and damping resistor 80 of the snubber circuit 70. Importantly, the voltage across the storage capacitor 60 is not applied to any of the switching elements 90, 92, 98, 100 which are included in the steering circuit 46.

This contrasts markedly with conventional energy storage and H-bridge circuitry, in which the full capacitor voltage is applied to one or more of the bridge switching elements. The effects of voltage applied to the bridge and associated leakage currents must be controlled to avoid deleterious effects to the ECG circuitry 24, the switching elements themselves and the patient.

The bridge designs shown in FIGS. 3A and 3B also contrast with conventional designs that require two storage capacitors, i.e. one for delivering high voltage defibrillation shocks and one for delivering lower voltage pacing pulses, and two therapy delivery circuits.

In current AED designs, circuit components such as relays or sparkgaps are used to isolate the patient from the bridge circuitry and/or the bridge circuitry from the energy storage capacitor. By avoiding application of the capacitor voltage to the bridge elements during stand-by operations, and thereby avoiding the associated leakage currents, the need for these additional circuit components (and associated control complexity) is eliminated. During ECG monitoring operations, the forward and reverse blocking characteristics of the SCRs 90, 92, 98, and 100 effectively isolate the patient 104 and the ECG circuit 24 from the rest of the circuitry of FIGS. 3A and 3B.

When the decision is made to deliver electrical energy to the patient 104, the $SCR_{LR}$ 100 and the $SCR_{UL}$ 90 are first turned on, and conduction is then initiated by switching on the GTO 62. Switching on the GTO 62 connects the positive terminal 64 of the storage capacitor 60 with ground potential, thereby pulling the voltage of the negative terminal 76 below ground. Current then flows from ground via the upper terminal 94, through the $SCR_{UL}$ 90, the patient 104, the $SCR_{LR}$ 100, the snubber circuit 70, and the current limiting resistor 68. After the voltage has decayed to a pre-selected value, such as approximately 1000 V, the current flow through the bridge is commutated by turning off the GTO 62. Following a brief pause, such as approximately 400 μs, the $SCR_{LL}$ 98 and $SCR_{UR}$ 92 are turned on, followed by the GTO 62 once again being switched on. Electrical energy is then discharged through the patient 104 to complete the biphasic pulse applied to the patient.

In the event of an over current condition (caused, for example, by a short circuit at the patient electrodes 22 shown in FIG. 1, the disarm SCR 74 shunts current away from GTO 62 or IGBT 63. In the circuit of FIG. 3A, the disarm SCR 74 shunts current away from GTO 62; current limiting resistor 68 limits the fault current to acceptable levels. In the circuit of FIG. 3B, the disarm SCR 74 shunts current away from IGBT 63 when the fault is sensed, IGBT 63 may then be turned off.

In some instances, electrical defibrillation may be performed on a patient by more than one defibrillator. In this case, the AED 10 of FIG. 1 may be connected to a patient while defibrillation energy from another external defibrillator is also applied to the patient. Referring then to FIGS. 3A and B, the circuit components must withstand high voltage and/or current applied to patient terminals 96 from a source other than the storage capacitor 60. In this case, the forward and reverse blocking characteristics of the SCRs 90, 92, 98, and 100 can be advantageously employed, and the required leakage parameters are considerably relaxed relative to those required during ECG monitoring in currently available AEDs.

Turning now to the operation of the alternate embodiment shown in FIG. 3B, during stand by operations, the capacitor 60 is fully charged, as described above, and no defibrillation energy is delivered to the patient resistance 104, pending completion of ECG monitoring by the ECG circuit 24. The ECG circuit 24 is typically ground referenced, as described above. During this time, the IGBT 63 and the disarm SCR 74 are off, with any leakage current through the IGBT being returned by the ground return diode 78 and damping resistor 80 of the snubber circuit 70. Again, the voltage across the storage capacitor 60 is not applied to any of the switching elements 90, 92, 98 and 100 which are included in the steering circuit 46.

When the decision is made to deliver pacing electrical energy to the patient 104, the capacitor is not fully charged: ideally being charged to 100–300 V. The switching elements 90 and 100 are turned on thus allowing current to be delivered across the patient 104 in one direction. The IGBT 63, which operates as a hard switch when in defibrillation mode (described above), is used in a linear mode as a control means for regulating pacing current (which is in the range of 10–200 mA) across the patient. The control block determines the voltage across $R_{SHUNT}$ and adjusts the IGBT 63 drive level accordingly. For example, if it is desirable to provide a pacing pulse of 150 mA and the voltage drop across $R_{SHUNT}$ is 5 mV, then the control block enables the IGBT to increase the current delivered from the capacitor until the voltage drop across RsHUNT is 7.5 mV.

An additional advantage of this circuit is that the biphasic nature of the bridge can be set to reverse pacing current and thereby reduce offset voltage induced in the electrodes. For example, a high energy, short time pacing pulse can be delivered in one direction by turning on switching elements 90 and 100, thereafter a second pacing pulse which is lower voltage and longer time can be delivered in the opposite direction by turning on switching elements 92 and 98.

The remaining operation of the circuit shown in FIG. 3B is identical to that described with reference to FIG. 3A.

Those skilled in the art will appreciate a number of advantages provided by the circuit topology of FIGS. 3A and 3B over conventional circuits for storing, controlling, and delivering defibrillation and pacing energy. Importantly, the switching elements included in the energy steering circuit 46 need not withstand the capacitor voltage during stand-by operations. Similarly, the circuit topology of FIGS. 3A and 3B provide for disarming the charged storage capacitor 60 or otherwise interrupting discharge operations without the resulting application of stresses, such as over current, over voltage, etc., to the circuit. For these reasons, among others, the component requirements for the steering circuit may be relaxed, and simpler, more robust bridge circuitry and associated control circuitry are made possible.

Figure 4:
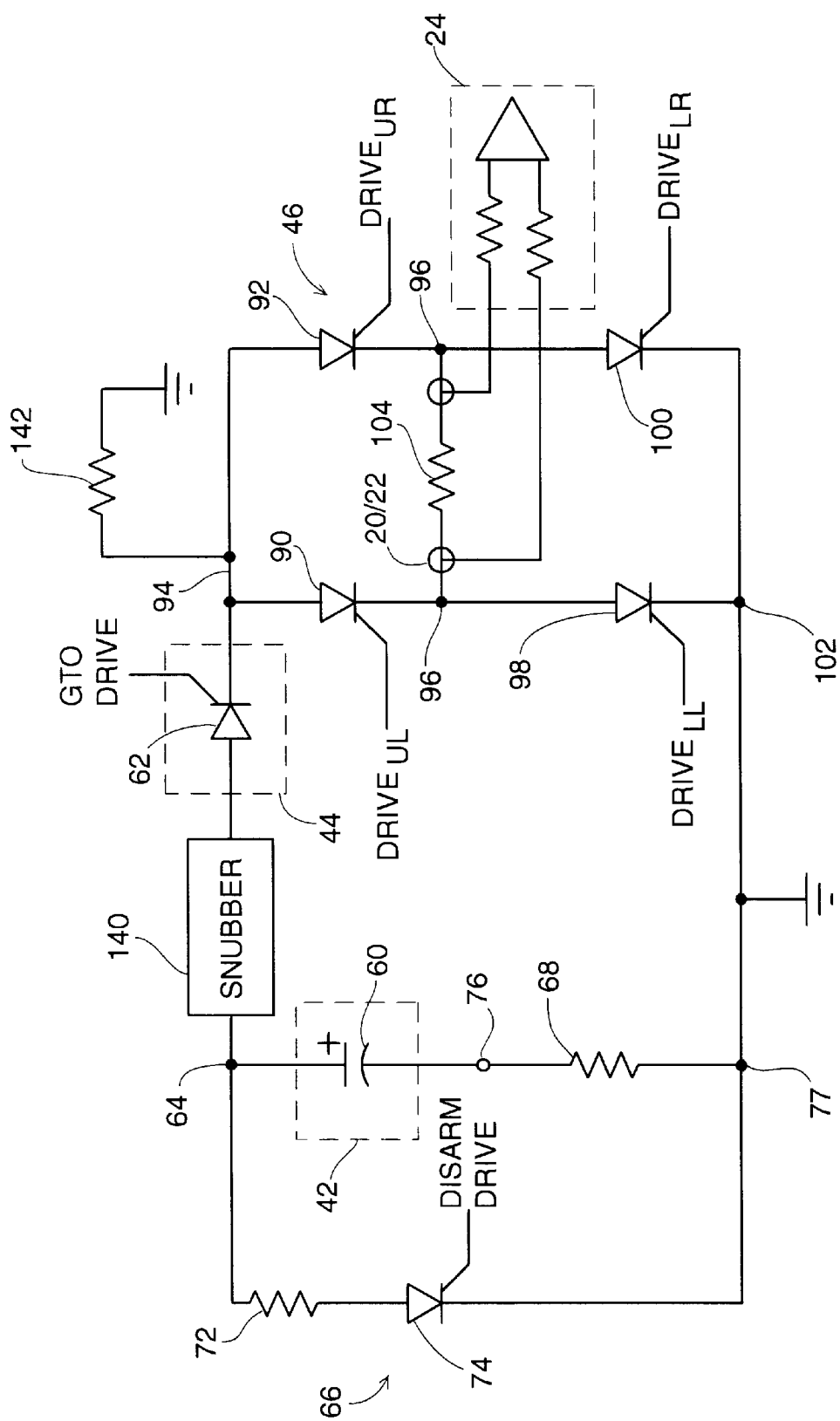
FIG. 4 is a schematic diagram depicting certain details of a second embodiment of the circuit of FIG. 2.

Those skilled in the art will understand that a number of switching elements could be substituted for the particular SCRs and GTO described above in connection with FIGS. 3A and 3B. However, such suitable circuit elements are not currently readily available, and FIGS. 3A and 3B depict embodiments in accordance with the present invention having switching elements which are, or soon will be, readily available and appropriate for use in an AED. In particular, suitable IGBTs and SCRs are currently available, and it is expected that suitable GTOs will soon be available. In the event such GTOs are not available, FIG. 4 depicts an alternative embodiment in which two insulated-gate bipolar transistors (IGBTs) are substituted for the GTO 62 of FIG. 3.

Those skilled in the art will appreciate that many of the advantages associated with the circuits described above in connection with FIG. 3 may be provided by other circuit configurations. In particular, the storage circuit 42, the discharge control circuit 44, and the steering circuit 46 are substantially connected in series, and alternative ordering of these units may be found in other embodiments of the present invention. For example, FIG. 4 shows a configuration in which the discharge control circuit 44 is coupled between the positive terminal 64 of the storage circuit 42 and the upper terminal 94 of the steering circuit 46. Correspondingly adapted snubber circuitry 140 may be connected between the discharge control circuit 44 and the storage circuit 42 to provide time rate-of-change of current limits and signal smoothing. A ground return resistor 142 is coupled between the upper terminal 94 and ground potential, to route leakage current through the discharge control circuit 44 away from the steering circuit 46 during stand-by operations. A suitable resistance value for the ground return resistor 142 is approximately 2 kΩ. Although many of the advantages described above in connection with FIG. 3 are likewise provided by the circuitry shown in FIG. 4, the discharge control circuit 44 is no longer ground referenced during defibrillator discharge operations, thereby making associated control circuitry more complex.

Figure 5A:
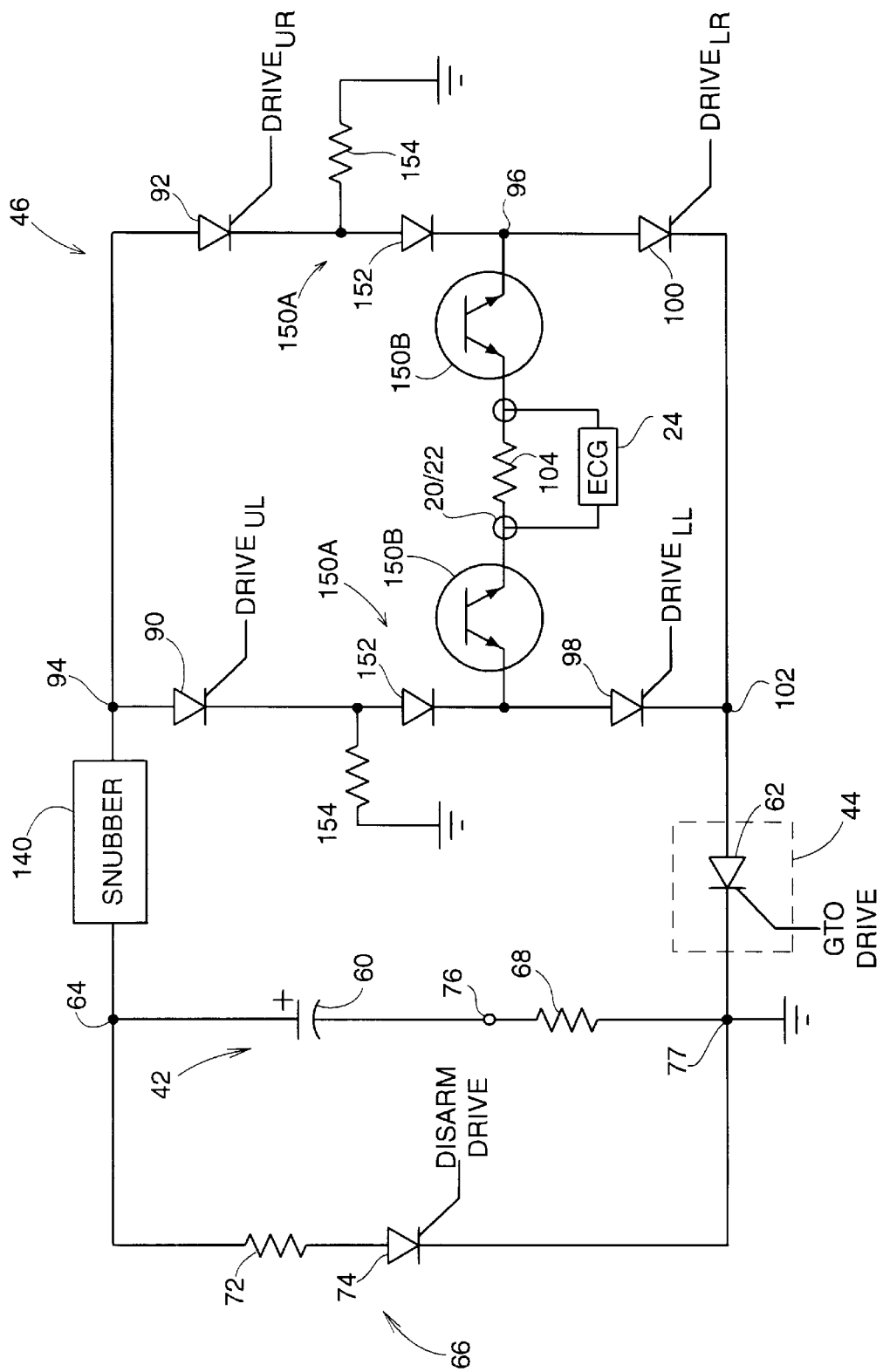
FIG. 5A is a schematic diagram depicting certain details of a third embodiment of the circuit of FIG. 2.

FIG. 5A depicts an embodiment that provides a way to keep leakage off the patient. Unlike FIGS. 3 and 4 which can be used for both pacing and defibrillation, FIG. 5 is optimally used for delivering defibrillation only.

The discharge control circuit 44 of FIG. 5 is coupled between the lower terminal 102 of the steering circuit 46 and the negative terminal 76 of the storage circuit 42. In this case, the control circuitry associated with the discharge control circuit 44 may be readily ground referenced. However, the high voltage of the storage circuit 42 is applied to switching elements within the steering circuit 46 during stand-by operations. Therefore, provision must be made within the steering circuit 46 to shunt associated leakage currents or otherwise isolate the patient 104 and ECG circuitry 24. Alternative approaches are shown in FIG. 5A as isolation circuits 150A and 150B. In the former, one of two diodes 152 is coupled between a corresponding one of the patient terminals 96 and the cathode of the corresponding upper SCR 90, 92. During ECG monitoring operations, the voltage at the patient terminal 96 is typically approximately 2–3 V, thereby reverse biasing the diodes 152. Ground return resistors 154 are then provided to route the leakage current passing through upper SCRs 90, 92. A suitable resistance value for each of the resistors 154 is approximately 10 kΩ. Alternatively, the isolation circuits 150B can each be coupled between a corresponding one of the patient terminals 96 and the connector 20, Each of the isolation circuits 150B may include a trigger diode or diac, as shown.

Figure 5B:
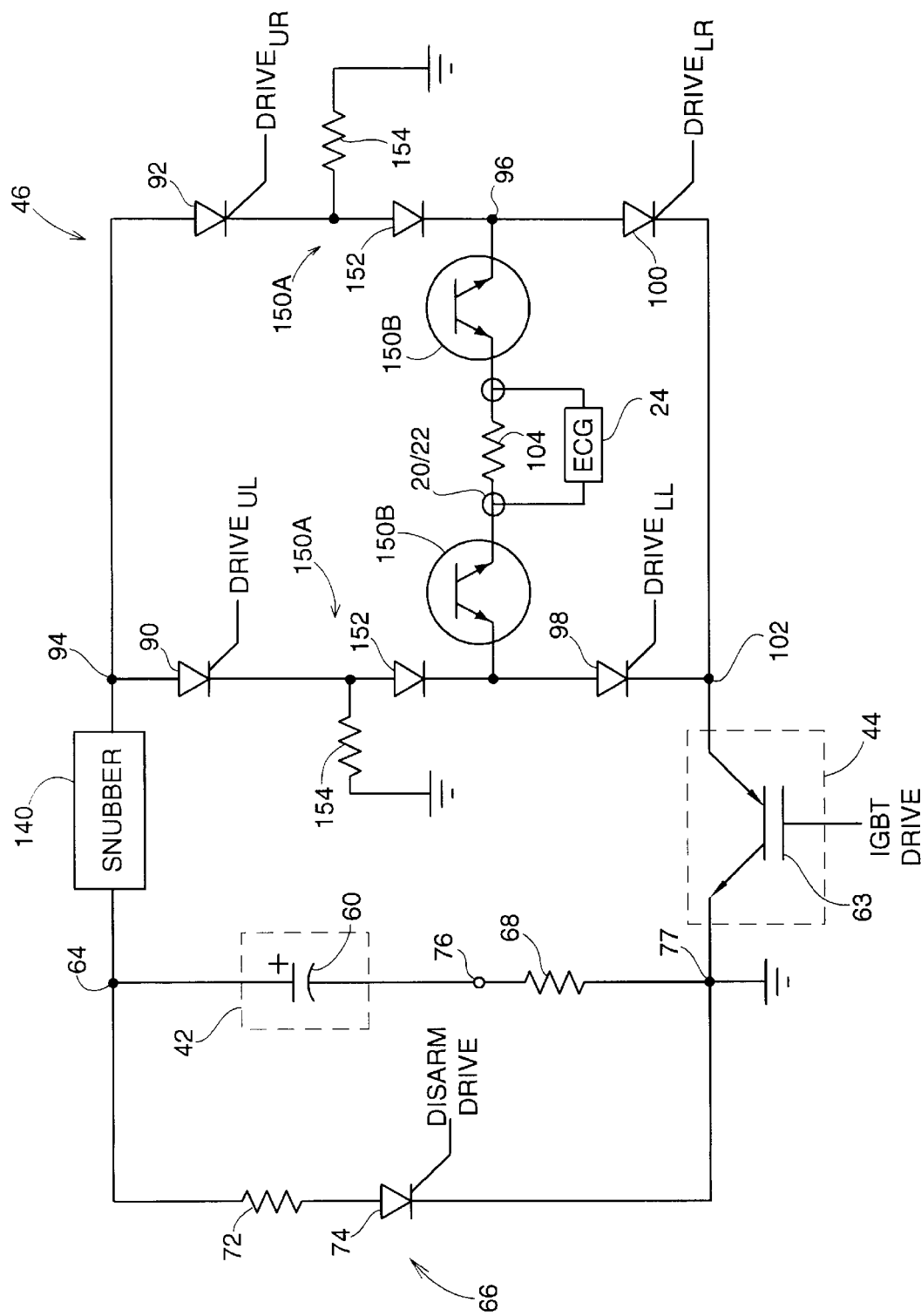
FIG. 5B is a schematic diagram depicting an alternative embodiment of the shown in FIG. 5A.

FIG. 5B depicts an alternative embodiment of the circuit shown in FIG. 5A wherein the GTO 62 has been replaced by IGBT 63.

Those skilled in the art will understand that certain of the circuits and components shown in FIGS. 1–5 have not been described in particular detail. In such case, the circuits and components are the type whose function and interconnection is well known in the art, and one skilled in the art would be able to use such circuits and components in the described combination to practice the present invention. The internal details of these particular circuits are not part of nor critical to the invention, and a detailed description of such internal circuit operation is therefore not required.

It will be appreciated that, while specific embodiments of the invention have been described herein for purposes of illustration, various modifications may be made without deviating from the spirit and scope of the invention. Those skilled in the art will understand that a number of suitable circuits, other than those particular ones described above, can be adapted to implement a high voltage delivery circuit in accordance with the present invention. Accordingly, the invention is not limited by the disclosed embodiments, but instead the scope of the invention is determined by the following claims.

What is claimed is:

1. A circuit for delivering high energy defibrillation pulses and low energy pacing pulses comprising:

a power source;

a storage circuit connected to the power source; and a control circuit for controlling the delivery of either high energy defibrillation pulses or low energy pacing pulses from the storage circuit to a patient.

2. A circuit according to claim 1 wherein the control circuit includes an electrically controlled switching element.

3. A circuit according to claim 1 wherein the control circuit includes an electrically controlled switching element coupling the storage circuit with a reference voltage.

4. A circuit according to claim 1, further comprising:

a steering circuit including a bridge circuit, coupled between a first terminal of the storage circuit and a first reference voltage; and wherein the control circuit includes an electrically controlled switching element coupling a second terminal of the storage circuit with a second reference voltage.

5. A circuit according to claim 4, further comprising a protection circuit coupling the storage circuit and the steering circuit and operable to limit the delivery of the electrical energy to the steering circuit.

6. A circuit according to claim 4 wherein the steering circuit is operable to deliver the electrical energy as a biphasic pulse to the patient.

7. A circuit according to claim 4, wherein the control circuit prevents voltage from being applied across the steering circuit after the storage circuit has been charged.

8. A circuit according to claim 1, further comprising a protection circuit coupled with the storage circuit and operable to selectively discharge the electrical energy stored therein.

9. A circuit according to claim 1, wherein a patient is isolated from charge leakage from the storage circuit.

10. An electrical energy delivery circuit for defibrillating a patient experiencing ventricular fibrillation, comprising:

a storage circuit having first and second terminals, the storage circuit operable to store electrical energy;

a bridge circuit coupled to the second terminal of the storage circuit and adapted for coupling with the patient and operable to deliver electrical energy to the patient at alternate polarities; and a switching circuit coupled with the storage circuit and operable to electrically connect the first terminal of the storage circuit with the bridge circuit to deliver the electrical energy to the patient.

11. An electrical energy delivery circuit according to claim 10, further comprising a disarm circuit coupled with the storage circuit and operable to electrically connect the first and second terminals to discharge the storage circuit.

12. An electrical energy delivery circuit according to claim 11 wherein the disarm circuit is connected to the first and second terminals of the storage circuit and includes a series-connected switching element and resistive element.

13. An electrical energy delivery circuit according to claim 10, further comprising a protection circuit coupled between the storage circuit and the bridge circuit, the protection circuit being operable to limit current flowing through the bridge circuit.

14. An electrical energy delivery circuit according to claim 10, further comprising a protection circuit coupled between the storage circuit and the bridge circuit, the protection circuit being operable to limit the time-rate-of-change of current flowing through the bridge circuit.

15. An electrical energy delivery circuit according to claim 10 wherein the bridge circuit is operable to direct a biphasic pulse to the patient.

16. An electrical energy delivery circuit according to claim 10 wherein the bridge circuit includes no more than four switching elements.

17. An electrical energy delivery circuit according to claim 10, wherein the switching circuit prevents voltage from being applied across the bridge circuit after the storage circuit has been charged.

18. An electrical energy delivery circuit according to claim 10, wherein a patient is isolated from charge leakage from the storage circuit.

19. In an electrical defibrillator having a storage circuit coupled with a steering circuit, the storage circuit for storing electrical energy and the steering circuit for directing the electrical energy to a patient, a method of delivering electrical energy to the patient, comprising the steps of:

electrically isolating the steering circuit from the defibrillation voltage;

charging the storage circuit to a defibrillation voltage;

forming a conducting path through the steering circuit to the patient; and electrically applying the defibrillation voltage to the conducting path.

20. A method according to claim 19 wherein the step of electrically applying the defibrillation voltage includes the step of connecting the storage circuit to a reference voltage.

21. A method according to claim 19 wherein the step of forming a conducting path includes the step of connecting the patient to a reference voltage.

22. A method according to claim 19 wherein the step of forming a conducting path includes the step of connecting the patient to a reference voltage through the steer ing circuit, and wherein the step of electrically applying the defibrillation voltage includes the step of connecting the storage circuit to the reference voltage.

23. A method according to claim 19, wherein a patient is isolated from charge leakage from the storage circuit.

24. In an electrical defibrillator having a storage circuit and a steering circuit, the storage circuit for storing electrical energy and having first and second terminals, and the steering circuit for directing the electrical energy to a patient, a method of delivering electrical energy to the patient, comprising the steps of:

coupling the steering circuit to the first terminal of the storage circuit;

charging the storage circuit;

forming an electrical path through the steering circuit to the patient; and connecting the second terminal of the storage circuit to the steering circuit to apply a potential difference to the patient.

25. A method according to claim 24 wherein, prior to performing the step of connecting the second terminal of the storage circuit to the steering circuit, the method includes the step of connecting the steering circuit to a reference voltage source, and wherein the step of connecting the second terminal of the storage circuit to the steering circuit includes the step of connecting the second terminal of the storage circuit to the reference voltage source.

26. A method according to claim 24 wherein the step of charging the storage circuit includes the step of producing a voltage at the second terminal greater than a voltage at the first terminal.

27. A method according to claim 24, further comprising the steps of:

detecting a fault condition; and in response to detecting the fault condition, discharging the storage circuit.

28. A method according to claim 27 wherein the step of discharging the storage circuit includes the step of dissipating the energy stored therein.

29. A method according to claim 27 wherein the step of discharging the storage circuit includes the step of electrically coupling the first and second terminals.

30. A method according to claim 27, further comprising the step of limiting current flow through the steering circuit.

31. A method according to claim 27, further comprising the step of limiting the time-rate-of-change of current flow through the steering circuit.

* * * * *